United States Patent
Kurosawa et al.

[11] Patent Number: 5,897,759
[45] Date of Patent: Apr. 27, 1999

[54] $NO_X$ SENSOR

[75] Inventors: Hideyuki Kurosawa; Masaharu Hasei, both of Kumagaya; Noboru Yamazoe, Kasuga; Norio Miura, Fukuoka, all of Japan

[73] Assignee: Kabushiki Kaisha Riken, Tokyo, Japan

[21] Appl. No.: 08/711,463

[22] Filed: Sep. 11, 1996

[51] Int. Cl.⁶ ............................................... G01N 27/407
[52] U.S. Cl. ........................... 204/424; 204/426; 205/781
[58] Field of Search ................................... 204/421–429; 205/781

[56] References Cited

U.S. PATENT DOCUMENTS

| | | | |
|---|---|---|---|
| 4,011,149 | 3/1977 | Nozik | 205/340 |
| 5,045,170 | 9/1991 | Bullock et al. | 205/626 |
| 5,273,628 | 12/1993 | Liu et al. | 204/296 |
| 5,397,442 | 3/1995 | Wachsman | 204/426 |
| 5,405,718 | 4/1995 | Hashemi | 429/218 |

FOREIGN PATENT DOCUMENTS

| | | |
|---|---|---|
| 61-184450 | 8/1986 | Japan . |
| 62-95456 | 5/1987 | Japan . |
| 1-150849 | 6/1989 | Japan . |
| 4-297862 | 10/1992 | Japan . |
| 8-5606 | 1/1996 | Japan . |
| 8-62174 | 3/1996 | Japan . |

OTHER PUBLICATIONS

Hideyuki Kurosawa et al., "Solid Electrolyte NOx Sensor Using Oxide Ion Conductor", The 18th Chemical Sensor Meeting, vol. 10, pp. 73–76 (1993) month unavailable.

Lawrenz et al, "Investigations on the determination of NO with galvanic $ZrO_2$ solid electrolyte cells", Fresenius J. Anal Chem, (1994) month unavailable, pp. 679–683.

Primary Examiner—T. Tung
Attorney, Agent, or Firm—Kubovcik & Kubovcik

[57] ABSTRACT

The present invention discloses a NO$x$ sensor consisting at least of a pair of the first and the second electrodes formed in touch with an ion conductive solid electrolyte; wherein at least the first electrode is selected from hybrid oxides having perovskite structure expressed by $MSnO_3$ (M is at least an element selected from Mg, Ca, Sr, Ba, Mn, Co, Ni, Zn and Cd, hybrid oxides having pseudo-perovskite structure expressed by $M_2SnO_4$ (M is at least an element selected from Mg, Ca, Sr, Ba, Mn, Co, Zn and Cd) or a substance containing said hybrid oxides and the second electrode is selected from a noble metal or a electro conductive ceramics which does not have electro conductivity in the atmosphere of NO$x$ and the concentration of NO$x$ in the test gas is detected by the change of the electromotive force between the first and second electrodes.

3 Claims, 5 Drawing Sheets

NO$_x$ SENSOR

BACKGROUND OF THE INVENTION

Field of the Invention The present invention relates to a sensor to detect NO$x$ concentration in an exhaust gas from combustion furnace and automobile engine, etc.

From the view point of the protection of an environment on the earth, reduction of NO$x$, especially NO, is required and for the achievement of this requirement, the development of a NO$x$ sensor, which can be applicable to the feed back control of combustion state and NO$x$ removal system or to monitoring oxidation and reduction catalyst of NO, is thought to be essential. A solid electrolyte sensor which detects NO$x$ concentration by the change of electromotive force corresponding to the change of NO$x$ concentration and a semiconductor sensor utilizing the change of the resistance of organic or inorganic semiconductor depending on NO$x$ concentration have been reported as NO$x$ sensors.

For example, the Japanese Patent Laid-Open Publication Nos. Sho 61-184450 and Hei 4-297862 disclose a solid electrolyte sensor using AgI and NASICON as a solid electrolyte and metal nitrate as an electrode. These sensors show relatively good sensitivity for NO$x$ in a temperature range from 100~300° C. However, the melting point of AgI used as a solid electrolyte and metal nitrate used as an electrode are low and it was very difficult to use the sensor in a condition exposed to a temperature above 500° C.

Zirconia is used in oxygen sensors as a thermal stable electrolyte at a high temperature. In a NO$x$ sensor using zirconia, it is reported that a good performance is obtained by using mixed salts of Ba(NO$_3$)$_2$ or Ba(NO$_3$)$_2$ with other salts as an electrode. (The 18th Chemical Sensor Meeting, vol.10, p.73~76, 1993). However, a long range stability is an issue due to the deliquescence property of Ba(NO$_3$)$_2$. A sensor using SnO$_2$, which is stable at a relatively high temperature as an electrode and zirconia as an electrolyte is reported, however, the detectable gas is methane, but not NO$x$.

A sensor using organic semiconductor phthalocyanine has been disclosed (The Japanese Patent Laid-Open Publication No. Sho 62-95456), however, the working temperature is limited by the decomposition temperature of phthalocyanine and it is impossible to mount the sensor directly in an exhaust gas at a high temperature. On the other hand, a relatively stable sensor at a high temperature using an oxide semiconductor has been disclosed. (The Japanese Patent Laid-Open Publication No. Hei 1-150849). However, there were issues that the sensitivity is lowered or null above 500° C., where the gas absorption on the surface of the semiconductor does not occur easily, since the semiconductor sensor detects the concentration of the gas through the change of the resistance caused by the absorption of the gas on the surface of the semiconductor.

SUMMARY OF THE INVENTION

The sensors according to the prior art could not be mounted in a smoke duct of an engine and a furnace directly due to the issues in the melting point and thermal stability of the materials constituting the sensor. Even when the mounting is possible, enough sensitivity was not obtained in a range of high temperature. The object of the present invention is to provide a NO$x$ sensor having thermal stability and enough sensitivity to NO$x$ in a range of high temperature.

The sensor of the present invention is a NO$x$ sensor consisting at least of a pair of electrodes formed in touch with an ion conductive solid electrolyte, wherein at least the first electrode is composed of hybrid oxides having perovskite or pseudo-perovskite structure or a substance containing said hybrid oxides.

DETAILED DESCRIPTION

Figure 1:
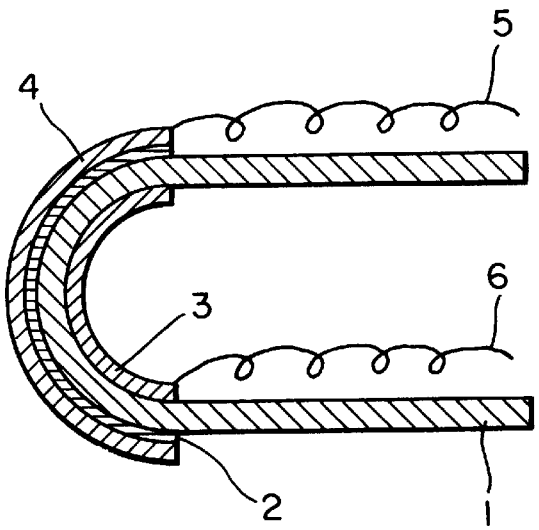
FIG. 1 is a cross section of a NO$x$ sensor of an example according to the present invention.

More concretely, the first electrode of the NO$x$ sensor according to the present invention is composed of a hybrid oxide having perovskite structure comprising metal M and Sn or Ti expressed by the general formula MSnO$_3$ or MTiO$_3$, wherein M is at least an element selected from the group consisting of Mg, Ca, Sr, Ba, Mn, Co, Ni, Cr (only for MTiO$_3$), Zn and Cd, hybrid oxides expressed by the general formula M$_2$SnO$_4$, wherein M is at least an element selected from the group consisting of Mg, Ca, Sr, Ba, Mn, Co, Zn and Cd or a substance containing these hybrid oxides.

The electrode composed of hybrid oxides having perovskite or pseudo-perovskite structure is formed by the screen printing process using a paste of hybrid oxide powder prepared either by the solid phase method (ceramic method, dropping thermal decomposition method, co-precipitation method, freeze-drying method, etc. or sintering. Plasma spraying method can be also used for the formation of the electrode.

Oxides of respective metal may be used as the starting material of hybrid oxides powder, however, there is a case that a mono phase of perovskite or pseudo-perovskite is easily obtained using metal salt of acetic acid, nitric acid, carbonic acid, phosphoric acid, sulfuric acid, etc., organic compounds and inorganic compounds of the respective metal. However, the starting material should be selected corresponding to the manufacturing method and metals other than the objective metal should not be involved in the structure.

Furthermore, the physical deposition method such as sputtering, laser ablation, ion beam deposition and ionplating or chemical deposition method such as plasma chemical vapour phase deposition method can be used for the formation. The electrode formation by these methods can be done either by the heat treatment of the membrane of the constituted metal formed before hand under oxygen or oxygen containing atmosphere or directly by controlling atmosphere at the formation.

The method of the formation of an electrode is not limited to the above mentioned methods and any method can be used so far as the method can form an electrode composed of hybrid oxides having perovskite or pseudo-perovskite structure. The first electrode is not limited to one composed of hybrid oxides, but can be one composed of a mixture with other oxides than said hybrid oxides. For example, it can be a mixture with $SnO_2$ or $TiO_2$. Furthermore, it can be a mixture with an element expressed by M. A mixture with oxides can be used so far as it does not counteract the change at the first electrode.

A mixture can be one wherein noble metals such as Au, Pt, etc. or electro conductive materials such as metals are dispersed in the electrode or one which is laminated on the electrode or buried in the electrode. In case it is a mixture with conductive materials, the mixture can function as a collector.

As a solid electrolyte, oxygen ion conductor such as zirconia ($ZrO_2$—$M_2O_3$ or $ZrO_2MO$, where M is Yb, Gd, Nd, Ca, Y, Mg and Hf), bismuth oxide ($Bi_2O_3$—$M_2O_3$ or —MO or $M_2O_5$, where M is Y, Gd, Nb, W, Sr, Ba) and cerium oxide ($CeO_2$—$M_2O_3$ or —$MO_2$, where M is Y and Sn) can be used.

A solid electrolyte can be constituted as either a separation wall or plate/rod structure. In the case that the solid electrolyte constitutes a separation wall, at least one pair of electrodes is formed on each side of the separation wall and in the case that it does not constitutes a separation wall, at least one pair of the electrode is formed at any place on the solid electrolyte.

The second electrode is composed of noble metals such as Pt, Ag, Au and Pd or conductive ceramics which do not change the conductivity in an atmosphere of NOx.

A sensor according to this invention is composed not only of a pair of electrodes, but also can be composed of a third electrode, for example carbonate electrode for the detection of $CO_2$ or CO gas and sulfate electrode for the detection of SOx gas, for the detection of other gases or removal of the effect of coexisting gases.

In the case that a solid electrolyte is constituted as a separation wall, the NOx concentration in the test gas is detected by the measurement of the electromotive force caused by the difference of the partial pressure of $NO_2$ and NO in both sides of the separation wall.

In a structure, wherein both of the paired electrodes are exposed in the gas without being separated by a solid electrolyte wall, NOx in the gas is detected by the measurement of the electromotive force caused by the difference in the reaction of NOx on the first electrode comprising hybrid oxides and the second electrode consisting of noble metals or electro conductive ceramics. Particularly, in this structure, it is possible to make a sensor which has no oxygen concentration dependency by equalizing the number of electrons involved in the reaction at the first and second electrodes.

For example, if the reaction with oxygen at the first electrode is four electrons reaction, it is possible to make a sensor, wherein the electromotive force between the first and second electrode does not change by adopting Pt as the second electrode which cause 4 electrons reaction with oxygen.

In an electromotive force type sensor composed of a pair of electrodes formed on a solid electrolyte to detect electropotential caused by the difference of the chemical potential between the electrodes, a solid electrolyte of transport number being close to 1 is used. One of the paired electrodes formed on a solid electrolyte as a detecting electrode reacts with the test gas existing around the surface of the electrode and the difference of the electromotive force is caused by the change of the chemical potential of the ion conductive carrier of a solid electrolyte against the chemical potential of the other electrode.

Many kinds of reactions are conceivable in the change of the chemical potential at the detecting electrode of NOx. For example, in case that the change of the chemical potential is caused by the reaction with the test gas, a selective catalytic activity for NOx is thought to be effective for the change of chemical potential. Oxygen deficiency in hybrid oxides caused by the reaction with NOx would be also effective. The electrode reaction on the first electrode has not been elucidated at present, the electromotive force is thought to be caused by the change of the chemical potential by reaction with NOx on hybrid oxides.

In these sensors, a heater can be optionally placed, if required.

Thus hybrid oxides having perovskite or pseudo-perovskite structure can be used as an electrode material of NOx sensor which is needed to be exposed to an exhaust gas at several hundreds°C. temerature or used at a high temperature. These hybrid oxides are not soluble in water and can work in an atmosphere containing water vapor.

From above view points, the inventors prepared a NOx sensor consisting of the first electrode which is composed of hybrid oxides expressed by the general formula $MSnO_3$ or $MTiO_3$, wherein M is at least an element selected from the group consisting of Mg, Ca, Sr, Ba, Mn, Co, Ni, Cr (only for $MTiO_3$), Zn and Cd, hybrid oxides expressed by the general formula $M_2SnO_4$, wherein M is at least an element selected from the group consisting of Mg, Ca, Sr, Ba, Mn, Co, Zn and Cd or a substance containing these hybrid oxides and found the sensor showed good response both for $NO_2$ and NO. Expecially, when $SrTiO_3$ (M is Sr in $MTiO_3$) is used as an electrode, it showed higher sensitivity to $NO_2$ than NO and hence it was possible to detect only $NO_2$ or only NO by the use in combination with a sensor having sensitivity both for NO and $NO_2$.

The present invention is concretely explained by the examples, however, the present invention is not limited to these examples.

Example 1

FIG. 1 shows a cross section of a NOx sensor of Example 1 according to the present invention. The solid electrolyte according to the example can be either zirconia, bismuth oxide, ceria, however, zirconia wholly or partially stabilized by yttria, calcia, selia or magnesia is preferred for the reason of thermal stability, thermal durability and material strength. A solid electrolyte is composed of Zirconia tube 1 closed at one end. At the outside of Zirconia tube 1, the first electrode 2 composed of $Zn_2SnO_4$ and an electric collector 4 composed of Au mesh and lead part 5 are connected. In the inside of Zirconia tube 1, the second electrode 3 is formed and connected with lead part 6. The NOx concentration in the test gas can be detected by the measurement of the difference of electric potential between lead part 5 and 6.

$Zn_2$ $SnO_4$ was prepared using ZnO and $SnO_2$ powder ad pulverizing sintered $Zn_2SnO_4$ at 1000° C. for 12 hrs. The sintered powder was molded by pressing in ø 70 mm~2 mm thickness. Using this mold as a target, the first electrode of $Zn_2SnO_4$ was formed on the stabilized zirconia by sputtering and the second electrode was prepared by drying and sintering of the coated Pt paste.

Figure 2:
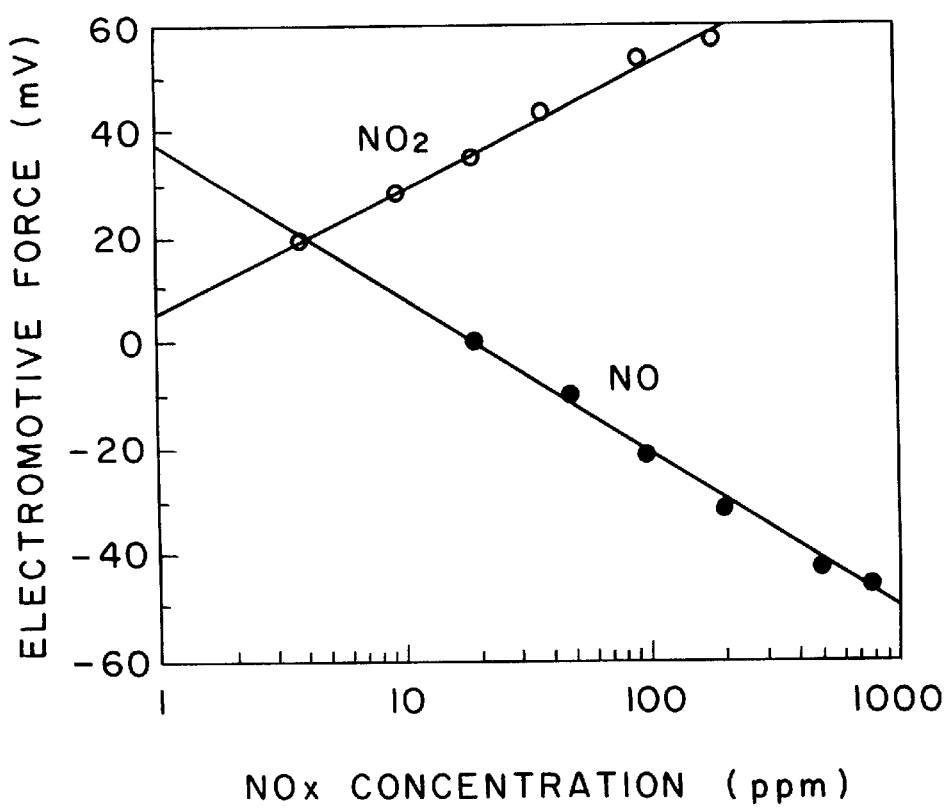
FIG. 2 is a figure showing the dependency of the change of the electromotive force of a NO$x$ sensor of an example according to the present invention on the NO$x$ concentration.

FIG. 2 shows the dependency of the change of the electromotive force on NOx concentration of this sensor. The change of the electromotive force of the sensor changes in proportion to the logarithm of the concentration of $NO_2$ and NO gas. The electromotive force increases in accordance with the increase of the concentration of $NO_2$ and decreases with the increase of the concentration of NO. The sensor of this example worked at 450~600° C. and showed the change of the electromotive force in accordance with the change of the concentration of NOx.

Example 2

Figure 3:
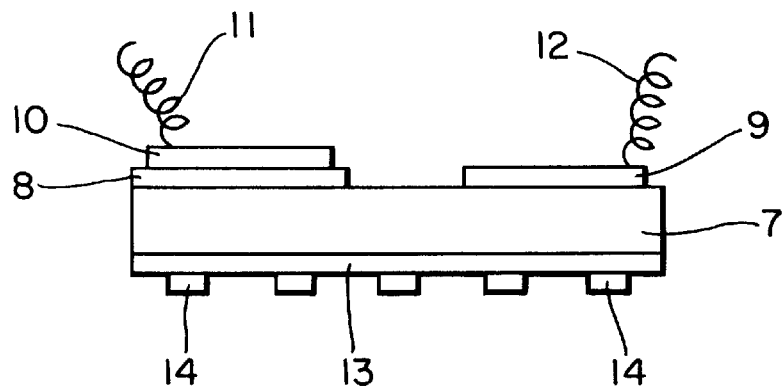
FIG. 3 is a cross section of a NO$x$ sensor of another example according to the present invention.

FIG. 3 shows a cross section of a NOx sensor of another example of the present invention. The solid electrolyte 7 is composed of zirconia stabilized by yttria. On a surface of the solid electrolyte, the first electrode 8 and the second electrode 9 are placed. The first electrode 8 is formed by sintering the coated paste consisting of hybrid oxides powder having perovskite or pseudo-perovskite structure or a mixture of hybrid oxides with other oxides. The second electrode 9 is composed of an electrode which does not respond to NOx and is Pt in this case. The first electrode 8 and the second electrode 9 are so called gas electrode and is formed as porous electrodes. An electric collector 10 of Au is placed on the first electrode 8 and the lead wire 11 and 12 of the electrode 8 and 9 are connected to the measurement circuit. On the back surface of the solid electrolyte, whereon above electrodes are formed, the heater 14 is placed through the insulation layer 13.

The solid electrolyte is not necessarily a plate, but can be a cylinder, a thin film prepared by sputtering or a thick film prepared by printing. The patterned shape is also not limited to a special shape.

The change of the electromotive force at the introduction of 100 ppm of $NO_2$ and 500 ppm of NO taking the value of the electromotive force under the atmospheric circumstance of 21% oxygen as a standard for a sensor consisting of the first electrode formed by sintering the coated paste of hybrid oxides powder or a mixture of hybrid oxides with other oxides at 1000° C. is shown in Table 1. Every sensor responded to $NO_2$ resulting in the increase of the electromotive force and to NO in the decrease of the electromotive force.

TABLE 1

The Change of the Electromotive Force corresponding to 100 ppm $NO_2$ and 500 ppm NO

| Electrode Material | The Chance of the Electromotive Force (mV) | |
| --- | --- | --- |
| | 100 ppm $NO_2$ | 500 ppm NO |
| $MgSnO_3$ | 17.3 | −20.5 |
| $Mg_2SnO_4$ | 17.6 | −7.0 |
| $CaSnO_3$ | 15.9 | −18.9 |
| $Ca_2SnO_4$ | 15.8 | −6.0 |
| $SrSnO_3$ | 16.3 | −19.9 |
| $Sr_2SnO_4$ | 16.5 | −5.0 |
| $BaSnO_3$ | 16.2 | −20.1 |
| $Ba_2SnO_4$ | 16.6 | −5.8 |
| $MnSnO_3$ | 40.5 | −40.4 |
| $Mn_2SnO_4$ | 18.5 | −23.8 |
| $Co_2SnO_4 + SnO_2$ | 43.7 | −41.6 |
| $Co_2SnO_4$ | 19.0 | −25.4 |

TABLE 1-continued

The Change of the Electromotive Force corresponding to 100 ppm $NO_2$ and 500 ppm NO

| Electrode Material | The Chance of the Electromotive Force (mV) | |
| --- | --- | --- |
| | 100 ppm $NO_2$ | 500 ppm NO |
| $NiSnO_3$ | 39.6 | −39.4 |
| $Zn_2SnO_4 + SnO_2$ | 40.1 | −41.5 |
| $Zn_2SnO_4$ | 48.9 | −57.4 |
| $CdSnO_3 + SnO_2$ | 5.5 | −19.5 |
| $Cd_2SnO_4$ | 29.5 | −30.5 |

Figure 4:
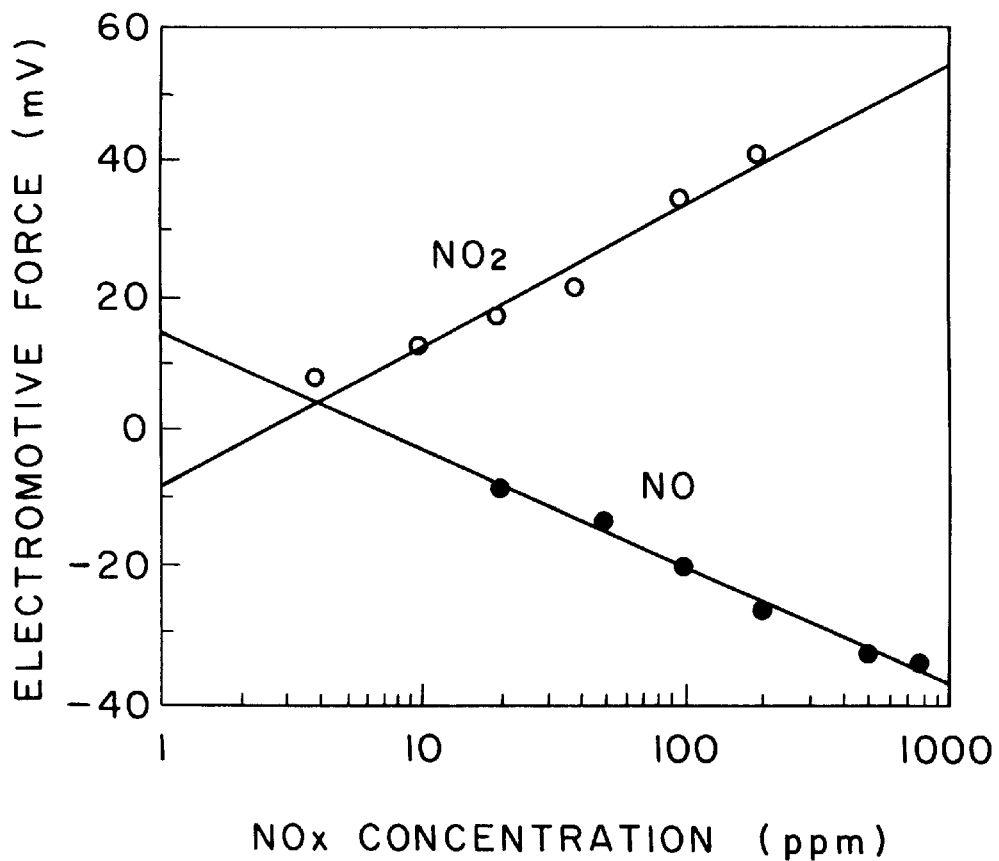
FIG. 4 is a figure showing the dependency of the change of the electromotive force of a NO$x$ sensor of another example according to the present invention on the NO$x$ concentration.
Figure 5:
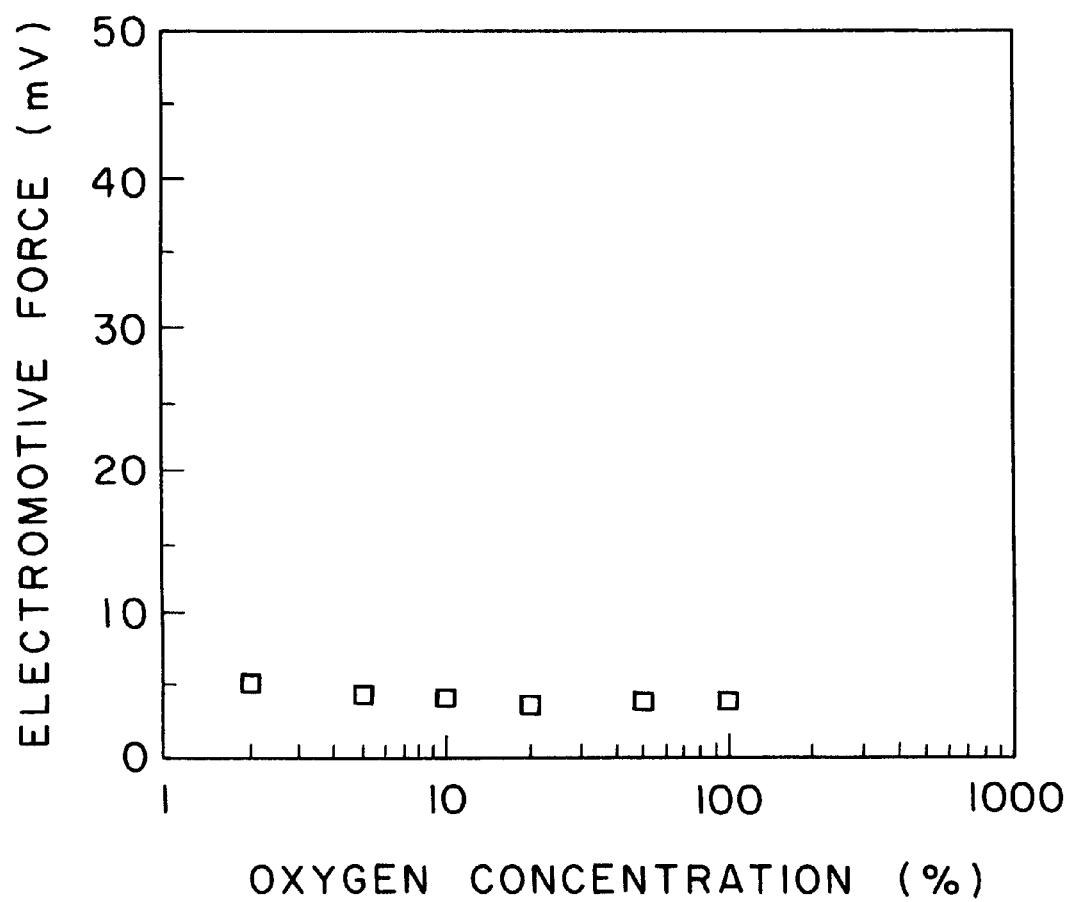
FIG. 5 is a figure showing the dependency of the electromotive force of a NO$x$ sensor of another example according to the present invention on the oxygen concentration.

FIG. 4 shows the dependency of the change of the electromotive force of a NOx sensor consisting of the first electrode composed of a mixture of $Co_2SnO_4$ and $SnO_2$ in an atmosphere of air at 500° C. In this sensor, the electromotive force changes also in proportion to the logarithm of the concentration of $NO_2$ and NO and the electromotive force increases in accordance with the increase of the concentration of $NO_2$ and decreases in accordance with the increase of the concentration of NO. Furthermore, in this sensor as is shown in FIG. 5, the electromotive force does not change even when the concentration of oxygen changed and it was elucidated that the sensor is not affected by the concentration of oxygen. The sensor worked at 450~600° C0 and showed the change of the electromotive force corresponding to NOx concentration.

Example 3

Figure 6:
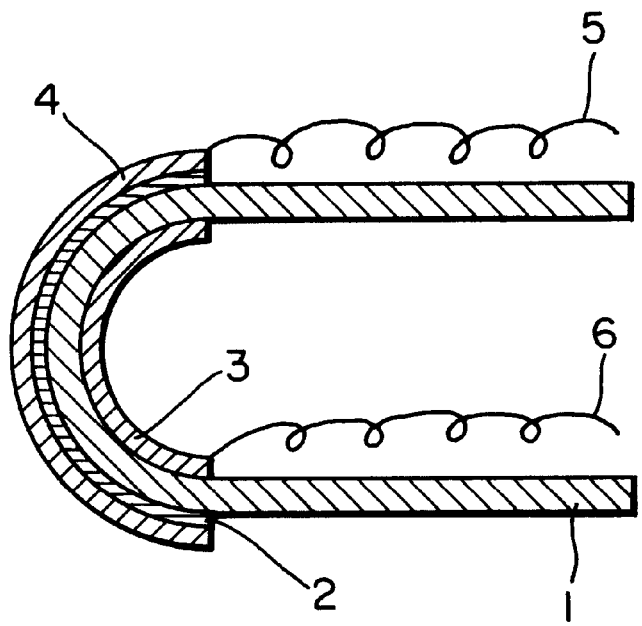
FIG. 6 is a cross section of a NO$x$ sensor of a third embodiment according to the present invention.

FIG. 6 shows a cross section of a NOx sensor of Example 3 according to the present invention. The solid electrolyte according to this example can be either zirconia, bismus oxide, ceria, however, zirconia wholly or partially stabilized by yttria, calcia, selia or magnesia is preferred for the reason of thermal stability, thermal durability and material strength. A solid electrolyte is composed of Zirconia tube 1 closed at one end. At the outside of Zirconia tube 1, the first electrode 2 composed of perovskite structure and an electric collector 4 composed of Au mesh and lead part 5 are connected. In the inside of Zirconia tube 1, the second electrode 3 is formed and connected with lead part 6. The NOx concentration in the test gas can be detected by the measurement of the difference of electro potential between lead part 5 and 6.

The change of the electromotive force at the introduction of 100 ppm of $NO_2$ and 500 ppm of NO taking the value of the electromotive force under the atmospheric circumstance of 21% oxygen as a standard for a sensor consisting of the first electrode formed by sintering the coated paste of hybrid oxides powder or a mixture of hybrid oxides with other oxide at 1000° C. Every sensors responded to $NO_2$ resulting in the increase of the electromotive force and to NO in the decrease of the electromotive force as is shown in Table 2.

TABLE 2

The Change of the Electromotive Force
corresponding to 100 ppm $NO_2$ and 500 ppm NO

| Electrode Material | The Chance of the Electromotive Force (mV) | |
|---|---|---|
| | 100 ppm $NO_2$ | 500 ppm NO |
| $MgTiO_3$ | 14.3 | −12.7 |
| $CaTiO_3$ | 18.1 | −13.3 |
| $SrTiO_3 + TiO_2$ | 58.2 | −12.0 |
| $BaTiO_3$ | 7.3 | −3.5 |
| $CrSnO_3$ | 21.7 | −26.2 |
| $ZnTiO_3 + ZnO + TiO_3$ | 41.3 | −38.4 |
| $CdTiO_3$ | 18.6 | −15.9 |

Example 4

Figure 7:
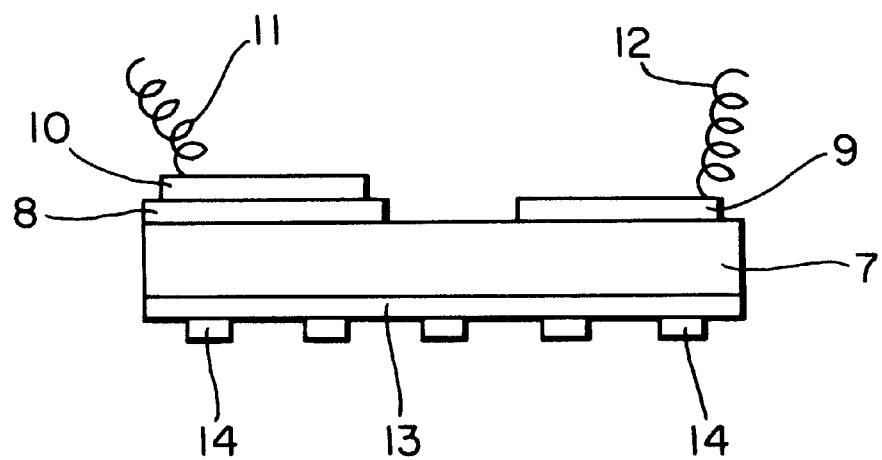
FIG. 7 is a cross section of a NO$x$ sensor of the other example according to the present invention.

FIG. 7 shows a cross section of a NO$x$ sensor of another example of the present invention. The solid electrolyte 7 is composed of zirconia stabilized by yttria. On a surface of the solid eletrolyte, the first electrode 8 and the second electrode 9 are placed. The first electrode 8 is formed by sintering the coated paste consisting of hybrid oxides powder having perovskite structure. The second electrode 9 is composed of an electrode which does not respond to NO$x$ and is Pt in this case. The first electrode 8 and the second electrode 9 are so called gas electrode and is formed as porous electrodes. An electric collector 10 of Au is placed on the first electrode 8 and the lead wire 11 and 12 of the electrode 8 and 9 are connected to the measurement circuit.

On the back surface of the solid electrolyte, whereon above electrodes are formed, the heater 14 is placed through the insulation layer 13.

The solid electrolyte is not necessary a plate, but can be a cylinder, a thin film prepared by sputtering or a thick film prepared by printing. The patterned shape is also not limited to a special shape.

Figure 8:
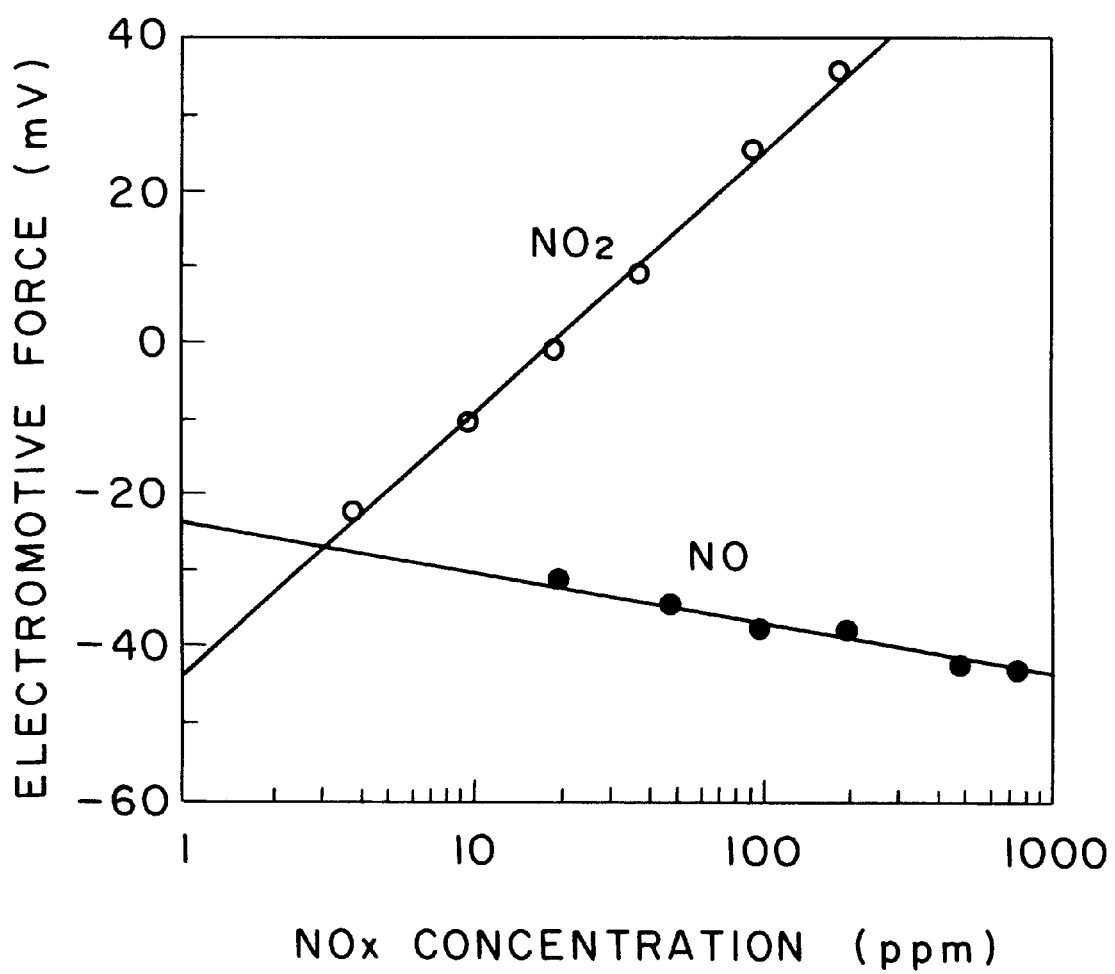
FIG. 8 is a figure showing a relation of the oxygen concentration and the electromotive force of a NO$x$ sensor.

FIG. 8 shows the dependency of the change of the electromotive force of a NO$x$ sensor consisting of the first electrode composed of a mixture of $SrTiO_3$ in an atmosphere of air at 500° C . In this sensor, the electromotive force changes also in proportion to the logarithm of the concentration of $NO_2$ and NO and the electromotive force increases in accordance with the increase of the concentration of $NO_2$ and decreases in accordance with the increase of the concentration of NO. The sensor worked at 450~600° C. and showed the electromotive force corresponding to NO$x$ concentration.

As explained above, a NO$x$ sensor according to the present invention can work stably even when exposed to exhaust gas containing water vapor of several hundred °C., because it is composed of hybrid oxides expressed by $MTiO_3$ having perovskite structure, which has high melting and decomposition temperature and is stable to water. And the present invntion can provide a NO$x$ sensor which responds well and detect both $NO_2$ and NO.

As many apparently widely different embodiments of the present invention can be made without departing from the spirit and scope thereof, it is to be understood that the invention is not limited to the specific embodiments thereof except as defined in the appended claims.

What is claimed is:

1. A $NO_x$ sensor consisting essentially of a pair of first and second electrodes in contact with a solid electrolyte, wherein said sensor is capable of detecting concentration of $NO_x$ in a gas by converting an amount of $NO_x$ concentration into an electromotive force level between the first and second electrodes, wherein the electromotive force linearly increases in response to an increase in terms of a logarithm of $NO_2$ concentration and linearly decreases in response to an increase in terms of a logarithm of NO concentration, characterized in that at least said first electrode is a compound oxide or a substance containing said compound oxide, said compound oxide being expressed by $M_2SnO_4$, where M is at least one element selected from the group consisting of, Mn, Co and Cd.

2. The $NO_x$ sensor of claim 1, wherein said electrodes are formed an opposing surfaces of said solid electrolyte or on a same surface of said solid electrolyte and both electrodes are exposed to said gas.

3. The NO$x$ sensor of claim 1, wherein said solid electrolyte is an oxygen conductive electrolyte.

* * * * *